(12) United States Patent
Clark

(10) Patent No.: US 12,029,610 B2
(45) Date of Patent: Jul. 9, 2024

(54) X-PLANE AND 3D IMAGING FOR ASYMMETRIC APERTURES

(71) Applicant: KONINKLIJKE PHILIPS N.V., Eindhoven (NL)

(72) Inventor: David Wesley Clark, Derry, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 419 days.

(21) Appl. No.: 16/338,884

(22) PCT Filed: Sep. 28, 2017

(86) PCT No.: PCT/EP2017/074581
§ 371 (c)(1),
(2) Date: Apr. 2, 2019

(87) PCT Pub. No.: WO2018/065282
PCT Pub. Date: Apr. 12, 2018

(65) Prior Publication Data
US 2021/0307721 A1 Oct. 7, 2021

Related U.S. Application Data

(60) Provisional application No. 62/434,517, filed on Dec. 15, 2016, provisional application No. 62/403,479, filed on Oct. 3, 2016.

(51) Int. Cl.
*A61B 8/12* (2006.01)
*A61B 8/00* (2006.01)
(Continued)

(52) U.S. Cl.
CPC .............. *A61B 8/12* (2013.01); *A61B 8/145* (2013.01); *A61B 8/4461* (2013.01);
(Continued)

(58) Field of Classification Search
CPC ......... A61B 8/12; A61B 8/4488; A61B 8/463; A61B 8/483; A61B 8/145; A61B 8/4461
See application file for complete search history.

(56) References Cited

U.S. PATENT DOCUMENTS 5,997,479 A   12/1999  Savord et al.
6,171,247 B1 *  1/2001  Seward .................... A61B 8/12
                                                        128/916
(Continued)

FOREIGN PATENT DOCUMENTS

WO    2015068073 A1    5/2015

OTHER PUBLICATIONS

Chen, et al., "A Front-end ASIC with Receive Sub-Array Beamforming Integrated with a 32 x 32 PZT Matrix Transducer for 3-D Transesophageal Echocardiography", 2016 Symposium on VLSI Circuits Digest of Technical Papers, 2 pages.

*Primary Examiner* — Colin T. Sakamoto
*Assistant Examiner* — Andrew W Begeman

(57) ABSTRACT

An intraluminal imaging device is provided. In one embodiment, the imaging device includes a flexible elongate member having a distal portion and a proximal portion. The flexible elongate member can be positioned within a vessel. The imaging device has an imaging assembly that can be mounted within the distal portion. The imaging assembly includes a side-looking array of imaging elements and a micro-beamformer IC that is coupled to the side-looking array of imaging elements. The micro-beamformer IC can control the array of imaging elements, can determine a first angle and a second angle, and can perform beam forming for the array of imaging elements. The micro-beamformer IC can receive the first imaging signals associated with a first plane (410) at the first angle (+45°), and the second imaging signals associated with a second plane (420) at the second
(Continued)

angle (−45°). In some embodiments, the first and second angles are selected to satisfy predetermined criteria.

13 Claims, 8 Drawing Sheets

(51) Int. Cl.
*A61B 8/08* (2006.01)
*A61B 8/14* (2006.01)

(52) U.S. Cl.
CPC ............ *A61B 8/4488* (2013.01); *A61B 8/463* (2013.01); *A61B 8/483* (2013.01)

(56) References Cited

U.S. PATENT DOCUMENTS

| | | | |
|---|---|---|---|
| 6,592,520 B1* | 7/2003 | Peszynski | A61B 8/12 600/459 |
| 2003/0028107 A1 | 2/2003 | Miller | |
| 2003/0060710 A1* | 3/2003 | Salgo | G01S 15/8925 600/443 |
| 2005/0281444 A1* | 12/2005 | Lundberg | A61B 8/08 382/128 |
| 2009/0030317 A1* | 1/2009 | Levy | A61B 8/4488 600/447 |
| 2011/0071395 A1* | 3/2011 | Miller | G01S 15/8925 600/439 |
| 2013/0281859 A1* | 10/2013 | Lause | G01S 15/8925 600/447 |
| 2014/0013849 A1* | 1/2014 | Gerard | G01S 7/52074 73/602 |
| 2017/0319180 A1 | 11/2017 | Henneken | |

\* cited by examiner

X-PLANE AND 3D IMAGING FOR ASYMMETRIC APERTURES

RELATED APPLICATIONS

This application is the U.S. National Phase application under 35 U.S.C. § 371 of International Application No. PCT/EP2017/074581, filed on Sep. 28, 2017, which claims the benefit of and priority to U.S. Provisional Application Nos. 62/403,479, filed Oct. 3, 2016, and 62/434,517, filed Dec. 15, 2016, which are incorporated by reference in their entireties.

TECHNICAL FIELD

The present disclosure relates generally to intraluminal imaging devices and, in particular, to array-based intraluminal imaging devices with an asymmetric aperture.

BACKGROUND

Diagnostic and therapeutic ultrasound catheters have been designed for use inside many areas of the human body. In the cardiovascular system, a common diagnostic ultrasound methods is intraluminal ultrasound imaging with intra-cardiac echocardiography (ICE) being a specific example of intraluminal imaging. Typically a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

Intraluminal ultrasound catheters are typically used in the large and small blood vessels (arteries or veins) of the body, and are almost always delivered over a guidewire having a flexible tip. Intraluminal imaging catheters such as ICE catheters are usually used to image heart and surrounding structures, for example, to guide and facilitate medical procedures, such as transseptal lumen punctures, left atrial appendage closures, atrial fibrillation ablation, and valve repairs. Commercially-available ICE imaging catheters are not designed to be delivered over a guidewire, but instead have distal ends which can be articulated by a steering mechanism located in a handle at the proximal end of the catheter. For example, an intraluminal imaging catheter such as an ICE catheter may be inserted through the femoral or jugular artery when accessing the anatomy, and steered in the heart to acquire images necessary to the safety of the medical procedures.

An ICE catheter typically includes imaging transducers for ultrasound imaging that generates and receives acoustic energy. The imaging core may include a lined array of transducer elements or transducer elements arranged in any suitable configuration. The imaging core is encased in an imaging assembly located at a furthest distal tip of the catheter. The imaging assembly is covered with acoustic adhesive materials. An electrical cable is soldered to the imaging core and extends through the core of the body of the catheter. The electrical cable may carry control core signals and echo signals to facilitate imaging of the heart anatomy. The assembly may provide rotational, 2-way, or 4-way steering mechanisms such that anterior, posterior, left, and/or right views of the heart anatomy may be imaged.

ICE imaging transducers are well known (e.g. Siemens Acunav, St. Jude ViewFlex). These transducers are introduced to the interior of the heart via a blood vessel by means of a catheter. ICE transducers may use a phased array sensor comprising many small individual transducers, each with a separate wire connecting the catheter to the imaging console. Up to 128 wires may be needed, leading to high cost, difficult manufacturing, and compromised image quality.

One type of intraluminal imaging catheter such as an ICE catheter (St. Jude Medical ViewFlex™ Intracardiac Ultrasound Deflectable catheter) has a distal articulation in a single plane (both directions), operated by a single wheel that rotates about the lengthwise axis of the handle. The wheel is turned to a specific position for the desired catheter shape, staying in place due to the inherent friction on the wheel mechanism. The catheter is torquable, and can be rotated with the handle to facilitate steering in a second plane. The motions required to simultaneously torque and rotate the catheter often require two-handed operation.

Another type of an intraluminal imaging catheter such as an ICE catheter (Siemens/ACUSON AcuNav™ Ultrasound Catheter) has an additional steering plane, and each steering plane is utilized by turning one of two corresponding wheels on the handle. These wheels rotate about the lengthwise axis of the handle. A third wheel, which also rotates about the lengthwise axis of the handle, is a locking mechanism for freezing each of the two steering wheels in its respective orientation. The entire catheter is also torquable, and can be rotated with the handle to facilitate steering in another plane. The two steering planes and catheter torquing allow a large combination of possible catheter configurations.

Intraluminal imaging catheters commonly provide steering through pullwires secured to the distal portions of the catheters near the imaging assemblies. The pullwires are also referred to as steering lines. The pullwires extend through the bodies of the catheters and are coupled to control wheels at handles of the catheters located at the proximal end of catheters. For example, a pair of pullwires may provide steering in a left-right plane and another pair of pullwires may provide steering in an anterior-posterior plane. Thus, the maneuvering or turning of a control wheel in turn actuates a corresponding pullwire to deflect the distal portion of a catheter in a corresponding direction.

Matrix array ultrasound transducers with symmetrical aperture dimensions have been used for 3D imaging and imaging multiple planes. By applying appropriate phases to the transducer signals, the matrix array may be steered and directed to desired planes to image the desired planes or image a 3D volume.

A problem with the current art intraluminal imaging transducers is that they may not have a symmetrical aperture and the aperture is longer in one dimension and shorter in the other. The asymmetric nature of the intraluminal imaging aperture causes different imaging resolutions in the commonly used x-plane images that acquire a first image expanding the longitudinal dimension of the intraluminal imaging aperture along the longer dimension and a second image expanding the transverse dimension of the intraluminal imaging aperture along the shorter dimension such that the second image is perpendicular to the first image. Also, this problem may create 3D images that have different resolution along different dimensions.

The demand for higher quality intraluminal images requires generating x-plane and 3D images that although the intraluminal imaging transducers may have an asymmetric aperture but the x-plane and 3D images essentially have the same resolution along different dimensions.

SUMMARY

Complicated surgeries are more frequently accomplished using minimally invasive procedures. A key in minimally invasive procedures is the ability to provide quality images within the body to assess, monitor, or guide the intervention. For example, the ability to image within the vasculature and the heart with essentially the same resolution as externally.

In some embodiments, matrix array ultrasound transducers with very asymmetrical aperture dimensions, such as a side-looking phased-array catheter transducer, have very compromised lateral resolution for imaging planes that are rotated far from the long aperture dimension. In particular, the asymmetry affects x-plane and 3D imaging. For example, one biplane that spans the transverse dimension of the transducer will have limited resolution because the aperture is shorter than the longer longitudinal dimension of the transducer. The current disclosure uses an x-shaped biplane that equally spans the face of the transducer, rather than a shorter transverse plane coupled with a longer longitudinal plane. This approach may minimally compromise resolution of the longitudinal dimension, but provides comparable resolution for both imaging planes.

In some embodiments, matrix array ultrasound transducers support x-plane imaging, with two simultaneous 2D imaging planes having rotations that are by default aligned with the aperture dimensions (0 degree and 90 degree). Typically one of the planes can be rotated or tilted by the user while the other remains aligned with the transducer aperture. Additionally, 3D volume rendering is acquired with multiple 2D planes, and the rotation of the acquisition planes is aligned with the aperture (0 degree and 90 degree). In some examples, MPR (multi-planar reformat) image planes are also extracted from the 3D volume data, and the MPR planes may be aligned with the aperture, although they may be translated/rotated by the user. X-plane or 3D mode is usually entered from a 2D mode where the plane is typically aligned with the aperture, so one of the x-plane or MPR images (or the front surface of the 3D volume) is the same as what was just being viewed.

In some examples, the aperture of a side-looking phased-array ultrasound transducer in a catheter, can be asymmetrical, because one dimension is constrained by the catheter diameter while the other dimension is as large as practical for resolution and sensitivity. Imaging tests have demonstrated that for a matrix array transducer with such an asymmetrical aperture, good lateral resolution may be maintained for 2D plane rotation up to 45 degree from the long dimension. The resolution is noticeably worse but acceptable up to 60 degree, and degrades rapidly from 60 degree to 90 degree.

The present disclosure solves that challenge of providing x-plane and 3D images using asymmetric apertures and provide essentially the same resolution in different dimensions, e.g., directions, by providing a different orientation when generating the x-plane and 3D images.

Embodiments of the present disclosure provide an intraluminal imaging device. The intraluminal imaging device includes a flexible elongate member such as a catheter that can to be positioned within a vessel. The flexible elongate member has a proximal portion and a distal portion. The intraluminal imaging device also includes an imaging assembly that can be mounted within the distal portion of the flexible elongate member. The imaging assembly can have a side-looking array of imaging elements. The imaging assembly also includes a micro-beamformer integrated circuit (IC) that can be coupled to the side-looking array of imaging elements. The micro-beamformer IC can control the side-looking array of imaging elements, can determine a first angle and a second angle based on a predetermined criterion, and can perform beam forming for the side-looking array of imaging elements. The micro-beamformer IC can receive the first imaging signals associated with a first plane at the first angle and the second imaging signals associated with a second plane at the second angle.

In some embodiments, the side-looking array imaging elements is an array of ultrasound imaging transducers that are directly flip-chip mounted to the micro-beamformer IC.

In one embodiment, a method of acquiring intraluminal images at two selectable planes includes transmitting and receiving imaging signals by a side-looking array of imaging elements positioned within a distal portion of an intraluminal imaging device. The method includes beamforming the first imaging signals received by the side-looking array of imaging elements and beamforming the second imaging signals received by the side-looking array of imaging elements. The beamforming is performed by a micro-beamformer integrated circuit (IC) coupled to the array of imaging elements. The first imaging signals are associated with a first plane at a first angle and the second imaging signals are associated with a second plane at a second angle. The first angle and the second angle are relative to the longitudinal direction of the aperture of the side-looking array of imaging elements. The method further includes generating a first image from the first imaging signals and generating a second image from the second imaging signals and determining the first angle and the second angle such that a predetermined criterion between the first image and the second image is satisfied.

In some embodiments, the method further comprises generating x-plane images and 3D volume images from the received plurality of imaging signals. In some embodiments, the micro-beamformer IC includes multiple microchannel delay lines, and the method further includes applying a plurality of predetermined delays to the imaging signals received by the side-looking array of imaging elements to generate beam forming.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
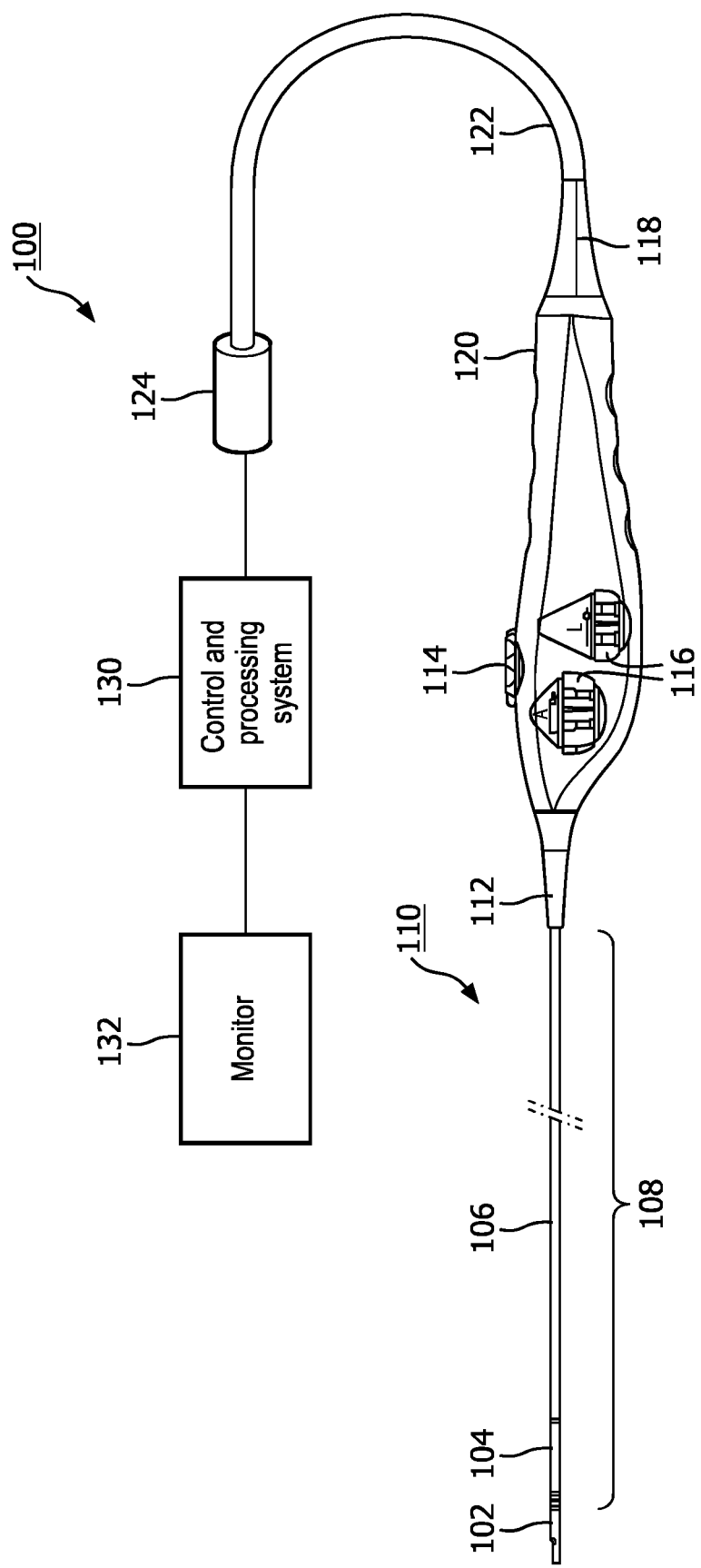
FIG. 1 is a schematic diagram of an intraluminal imaging system according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ICE system is described in terms of intraluminal imaging, it is understood that it is not intended to be limited to this application. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal imaging system 100 according to embodiments of the present disclosure. The system 100 may include an intraluminal imaging device 110, a connector 124, a control and processing system 130, such as a console and/or a computer, and a monitor 132. The intraluminal imaging device 110 includes an imaging assembly 102 at the tip of a flexible elongate member 108, and a handle 120. The flexible elongate member 108 includes a distal portion 104 and a proximal portion 106. The distal end of the distal portion 104 is attached to the imaging assembly 102. The proximal end of the proximal portion 106 is attached to the handle 120 for example, by a resilient strain reliever 112, for manipulation of the intraluminal imaging device 110 and manual control of the intraluminal imaging device 110. The imaging assembly 102 can include an imaging core with ultrasound transducer elements and associated circuitry. The handle 120 can include actuators 116, a clutch 114, and other steering control components for steering the intraluminal imaging device 110, such as deflecting the imaging assembly 102 and the distal portion 104, as described in greater details herein.

The handle 120 is connected to the connector 124 via another strain reliever 118 and a connection cable 122. The connector 124 may be configured in any suitable configurations to interconnect with the control and processing system 130 and the monitor 132 for processing, storing, analyzing, manipulating, and displaying data obtained from signals generated by the imaging core at the imaging assembly 102. The control and processing system 130 can include one or more processors, memory, one or more input devices, such as keyboards and any suitable command control interface device. The control and processing system 130 can be operable to facilitate the features of the intraluminal imaging system 100 described herein. For example, the processor can execute computer readable instructions stored on the non-transitory tangible computer readable medium. The monitor 132 can be any suitable display device, such as liquid-crystal display (LCD) panel or the like.

In operation, a physician or a clinician advances the flexible elongate member 108 into a vessel within a heart anatomy. The physician or clinician can steer the flexible elongate member 108 to a position near the area of interest to be imaged by controlling the actuators 116 and the clutch 114 on the handle 120. For example, one actuator 116 may deflect the imaging assembly 102 and the distal portion 104 in a left-right plane and the other actuator 116 may deflect the imaging assembly 102 and the distal portion 104 in an anterior-posterior plane, as discussed in greater details herein. The clutch 114 provides a locking mechanism to lock the positions of the actuators 116 and in turn the deflection of the flexible elongate member while imaging the area of interest.

The imaging process may include activating the ultrasound transducer elements on the imaging assembly 102 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the control and processing system 130 where the ultrasound image is reconstructed and displayed on the monitor 132. In some embodiments, the processing system 130 can control the activation of the ultrasound transducer elements and the reception of the echo signals. In some embodiments, the control and processing system 130 and the monitor 132 may be part of the same system.

The system 100 may be utilized in a variety of applications such as transseptal lumen punctures, left atrial appendage closures, atrial fibrillation ablation, and valve repairs and can be used to image vessels and structures within a living body. Although the system 100 is described in the context of intraluminal imaging procedures, the system 100 is suitable for use with any catheterization procedure, e.g., ICE. In addition, the imaging assembly 102 may include any suitable physiological sensor or component for diagnostic, treatment, and/or therapy. For example, the imaging assembly can include an imaging component, an ablation component, a cutting component, a morcellation component, a pressure-sensing component, a flow-sensing component, a temperature-sensing component, and/or combinations thereof.

In some embodiment, the intraluminal imaging device 110 includes a flexible elongate member 108 that can be positioned within a vessel. The flexible elongate member 108 having a distal portion 104 and a proximal portion 106. The intraluminal imaging device 110 includes an imaging assembly 102 that is mounted within the distal portion 104 of the flexible elongate member 108.

In some embodiments, the intraluminal imaging system 100 is used for generating 2D and 3D images. In some examples, the intraluminal imaging system 100 is used for generating x-plane images at two different viewing directions perpendicular to each other.

Figure 2:
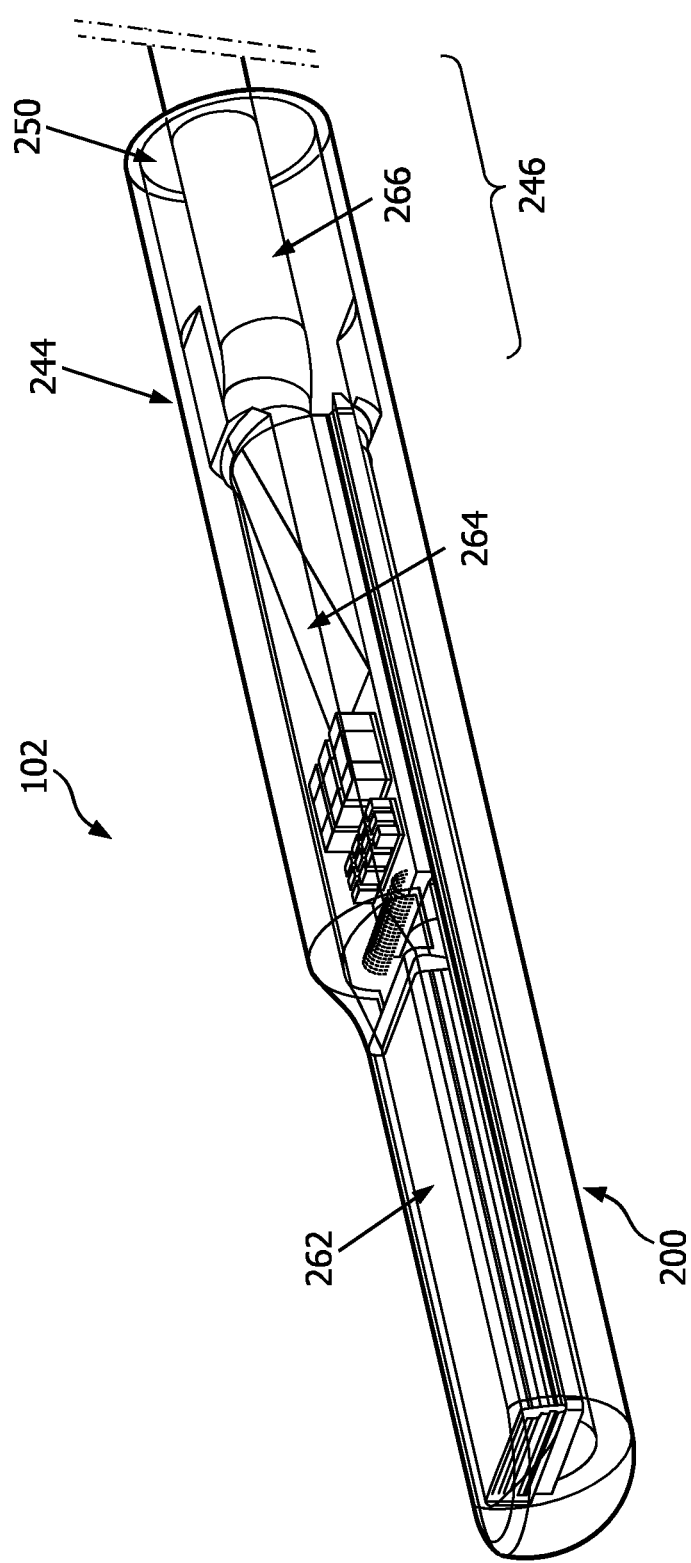
FIG. 2 is a perspective view of an imaging assembly according to aspects of the present disclosure.

FIG. 2 is a perspective view of the imaging assembly 102 positioned for coupling according to embodiments of the present disclosure. The imaging assembly 102 is illustrated with the imaging core 262 in position within the tip member 200. The imaging core 262 is coupled to the electrical cable 266 via the electrical interconnection 264. The electrical cable 266 extends through the alignment portion 244 and the interface portion 246 of the inner cavity 250. The electrical cable 266 can further extend through the flexible elongate member 108 as shown in FIG. 1.

The configuration and structure of the tip member 200 described above provide several benefits such as safe and easy delivery for catheterization, improved tensile strength for steering or navigation, consistent or automatic alignment, and improved image quality. For example, the outer geometry of the tip member 200 is configured to provide smooth surfaces and smooth edges with small radii. The smooth edges reduce friction when the tip member 200 traverses a vessel during insertion. The smooth surfaces prevent tears and/or damages to tissue structures during the insertion. In addition, the smooth edges and smooth surfaces can facilitate crossing of a septum or other anatomical feature during a catheterization procedure. The material type and the wall thickness of the tip member 200 are selected to minimize acoustic distortion, attenuation, and/or reflection. The internal geometry of the tip member 200 is configured to facilitate alignment during manufacturing. The tip member 200 can also include other features, for example, a guidewire lumen, holes, or other geometry to accommodate additional devices or features such as pressure sensors, drug delivery mechanisms, and/or any suitable interventional features.

Figure 3:
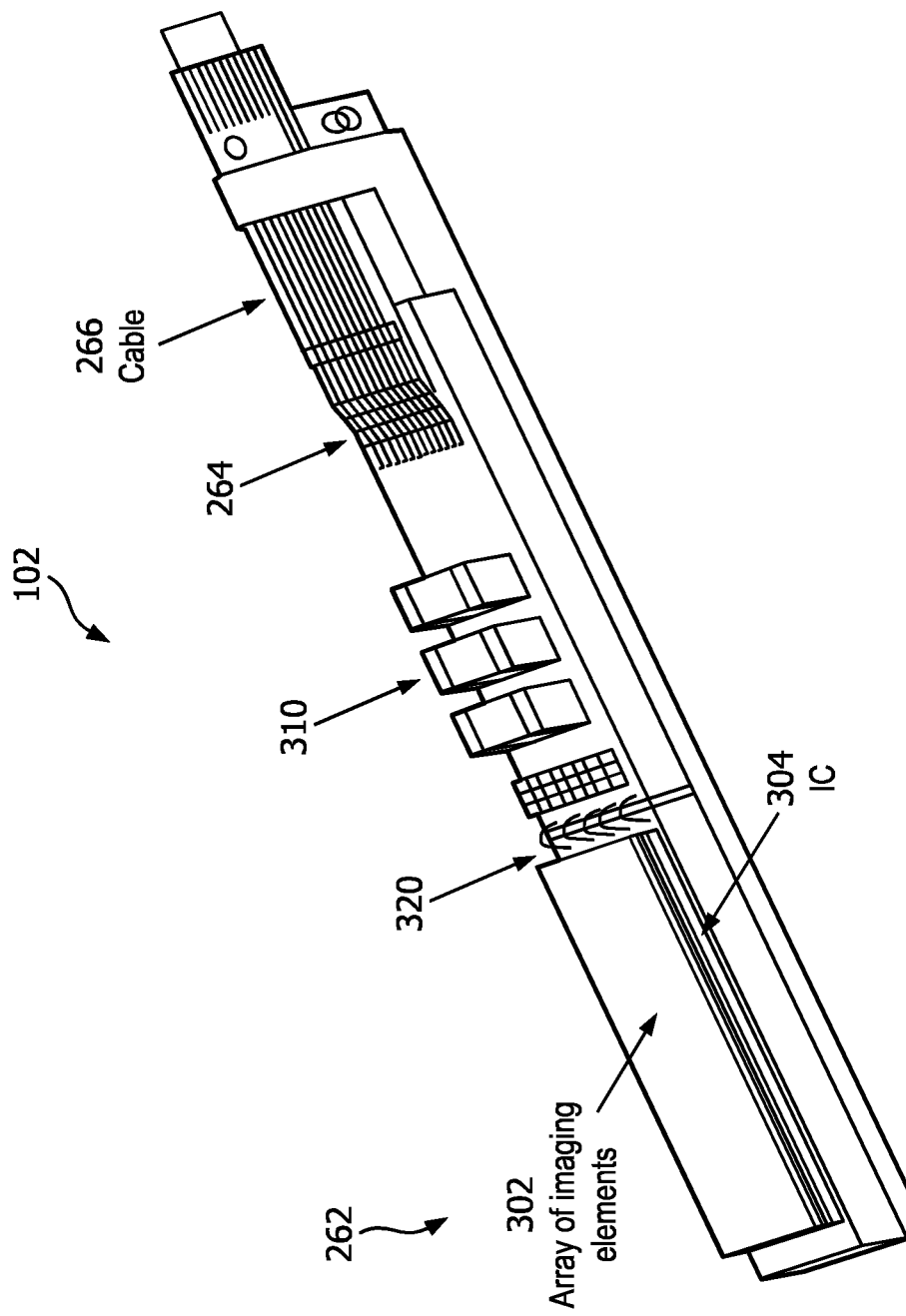
FIG. 3 is a top view of a tip member according to aspects of the present disclosure.

FIG. 3 is a top view of an imaging assembly 102 according to embodiments of the present disclosure. The imaging assembly 102 is illustrated with the imaging core 262 having an array of imaging elements 302 and micro-beamformer IC 304 coupled to the array of imaging elements 302. The imaging assembly 102 also shows the electrical cable 266 coupled to the electrical interconnection 264. In some examples, the electrical cable 266 is coupled through an interposer 310 to the micro-beamformer IC 304. In some examples the interposer 310 is connected to the micro-beamformer IC 304 through wire bonding 320. In some examples, the imaging assembly 102 is configured such that the electrical cable 266 is directly coupled to the micro-beamformer IC 304.

In some examples, imaging assembly 102 includes an array of imaging elements 302 in the form of an array of more than 800 imaging elements. In this regard, the imaging elements 302 may be arranged in a 2-dimensional array having a length greater than width such that more imaging elements 302 extend along the length of the array than across the width. As a result, the array of imaging elements 302 may have an asymmetrical aperture. In some embodiments, the array of imaging elements 302 is an array of ultrasound imaging transducers that are directly flip-chip mounted to the micro-beamformer IC 304. The transmitters and receivers of the ultrasound imaging transducers are on the micro-beamformer IC 304 and are directly attached to the transducers. In some examples, mass termination of the acoustic elements are done at the micro-beamformer IC 304.

In some embodiments, the micro-beamforming IC 304 lies directly underneath the array of acoustic elements 302 and is electrically connected to them. The array acoustic elements 302 may be piezoelectric or micromachined ultrasonic transducer (MUT) elements. Piezoelectric elements typically would be attached to the IC by flip-chip mounting an assembly of acoustic layers and sawing into individual elements. MUT elements may be flip-chip mounted as a unit or grown directly on top of the micro-beamforming IC 304. In some examples, the cable bundle may be terminated directly to the micro-beamforming IC 304, or may be terminated to an interposer 310 of suitable material such as a rigid or flexible printed circuit assembly. The interposer 310 may then be connected to the micro-beamforming IC 304 via any suitable means such as wire bonding 320.

Figure 4B:
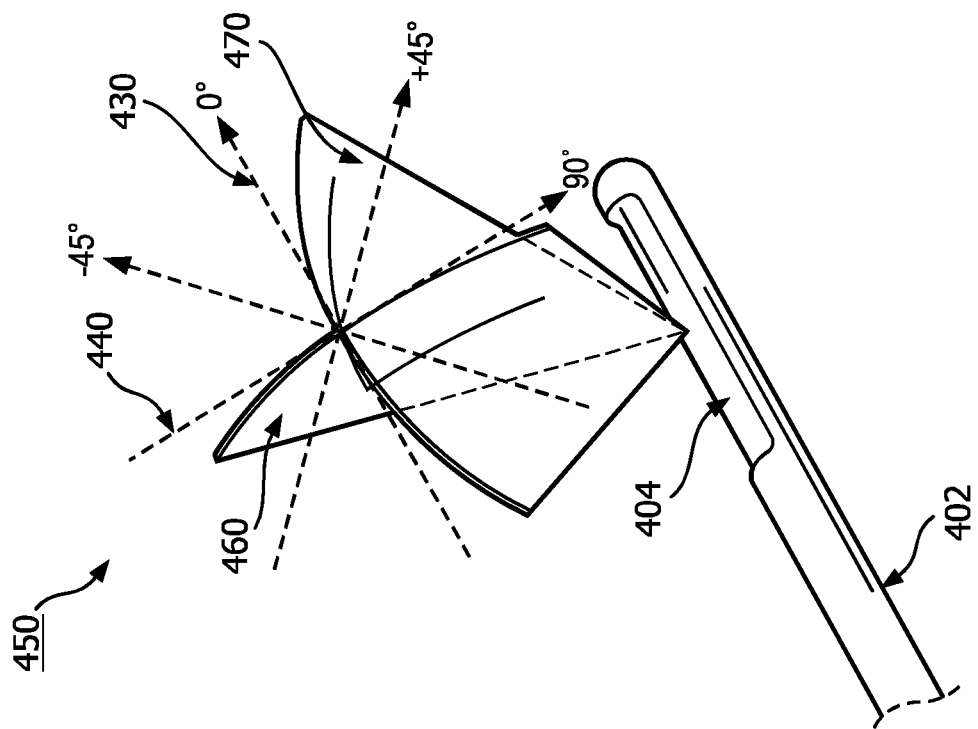
FIG. 4B is a schematic diagram illustrating two imaging planes extending coplanar with and at a right angle relative to a longitudinal axis of an asymmetric aperture of an imaging array according to aspects of the present disclosure.
Figure 4A:
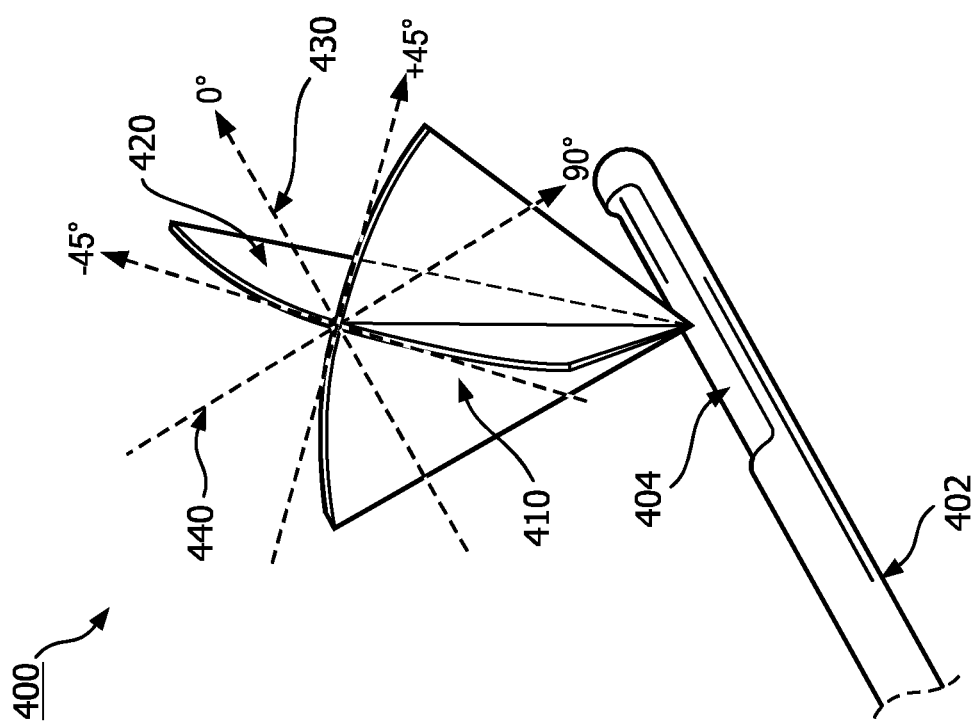
FIG. 4A is a schematic diagram illustrating two imaging planes extending at oblique angles relative to a longitudinal axis of an asymmetric aperture of an imaging array according to aspects of the present disclosure.

FIG. 4A is a schematic diagram 400 illustrating two imaging planes extending at oblique angles relative to a longitudinal axis of an asymmetric aperture of an imaging array according to aspects of the present disclosure. In particular, FIG. 4A shows imaging planes 410 and 420 extending at +45 degree and −45 degree angles, respectively, relative to a longitudinal axis 430 of the aperture 404. In other embodiments, the imaging planes 410 and 420 may extend at other oblique angles relative to the longitudinal axis 430 and/or a short axis 440 of the aperture 404 that extends perpendicular to the longitudinal axis 430. In some instances, the imaging planes 410 and 420 are at perpendicular angles relative to one another to facilitate x-plane and/or 3D imaging. In some instances, the imaging planes 410 and 420 extend at an oblique angle relative to one another. The diagram 400 shows the catheter tip 402 consistent with the tip 200 in FIG. 2 and also shows the aperture 404 of the array of imaging elements, which are arranged in a two-dimensional rectangular array. However, the diagram 400 can be representative of any asymmetric aperture of an imaging array for intraluminal imaging.

FIG. 4B is a schematic diagram 450 illustrating two imaging planes extending coplanar with and at a right angle, respectively, relative to a longitudinal axis of an asymmetric aperture of an imaging array. In particular, FIG. 4B shows imaging planes 460 and 470 extending at +90 degree and 0 degree angles, respectively, relative to the longitudinal axis 430 of the aperture 404 of the array of imaging elements.

Figure 5:
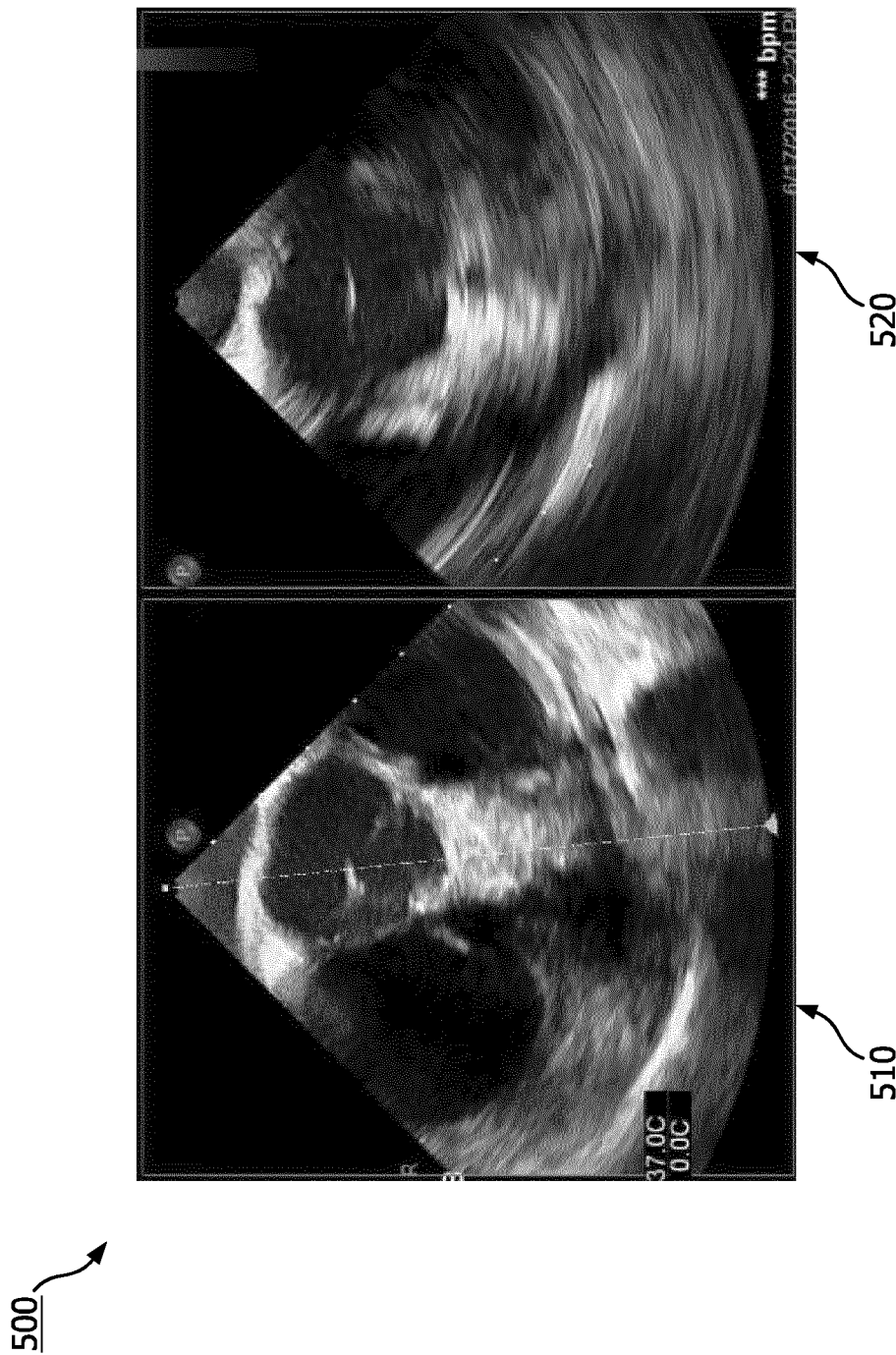
FIG. 5 shows ultrasound images at 0 degree and 90 degree planes relative to an asymmetric aperture of an imaging array according to aspects of the present disclosure.

FIG. 5 shows x-plane images at 0 degree and 90 degree. The images 500 are side by side images from 0 degree and 90 degree views, with the 0 degree view image 510 being on the left. As shown the image 510, 0 degree view, has a better resolution compared with the 90 degree view image 520 on the right.

Figure 6:
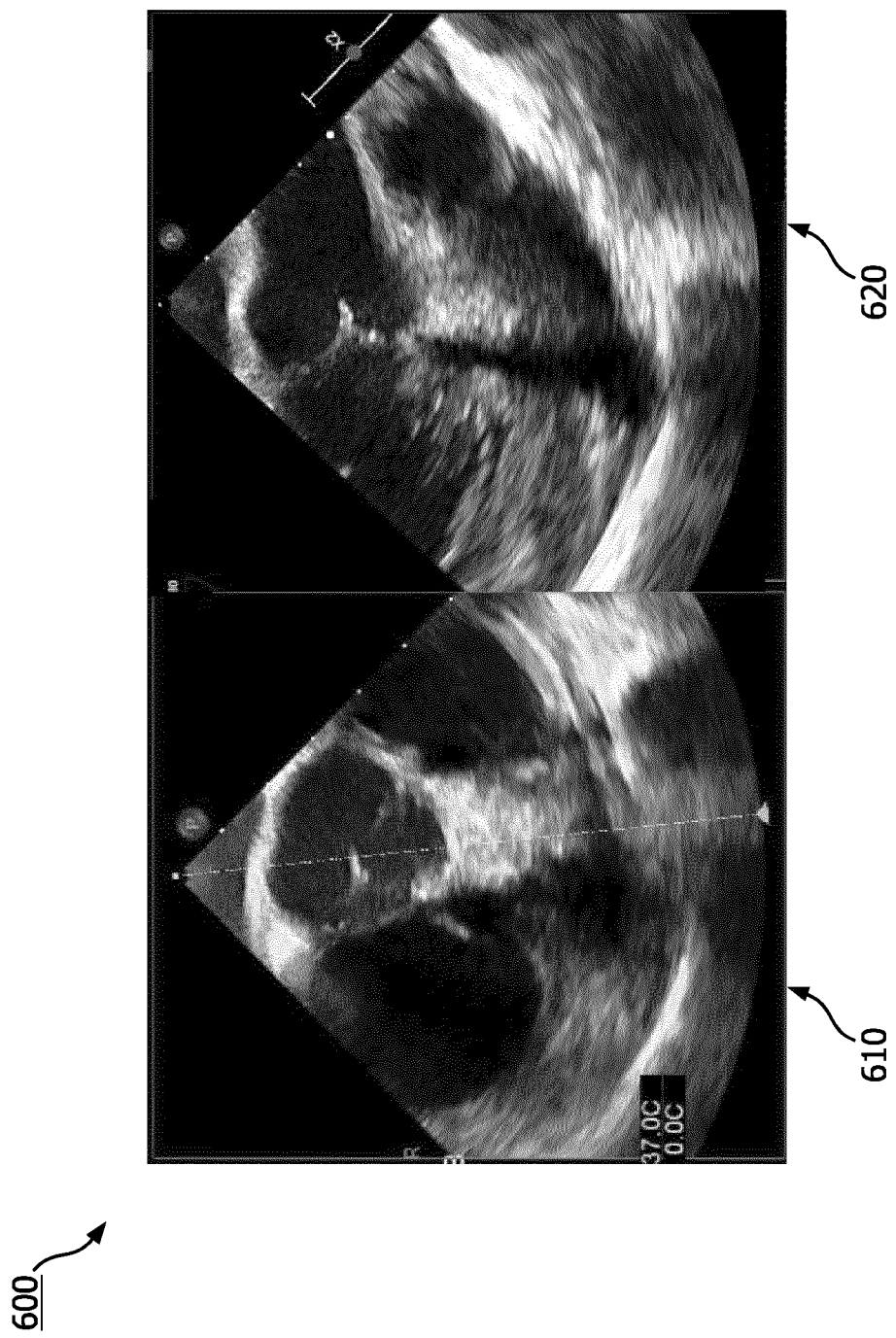
FIG. 6 shows ultrasound images at 0 degree and +45 degree planes relative to an asymmetric aperture of an imaging array according to aspects of the present disclosure.

FIG. 6 shows x-plane images at 0 degree and +45 degree. The images 600 are side by side images from 0 degree and +45 degree views, with the 0 degree view image 610 being on the left. As shown the 0 degree view image 610 and the +45 degree view image 620 have a comparable resolution. In some examples when displaying one or both of the +45 degree view and the −45 degree view images, one of the 0 degree view or the 90 degree view images is also displayed alongside of them to mentally help the view to realize the orientation.

Figure 7:
FIG. 7 shows a 3D volume image according to aspects of the present disclosure.

FIG. 7 shows a 3D volume image 710. The image 710 is a 3D volume image similar to a volume image between −45 degree and +45 degree. In some examples, the acquisition planes are at +45 degree and for each acquisition, the acquisition plane is moved orthogonal to the +45 degree plane, i.e., moves in the −45 degree plane. In some other examples, the acquisition planes are at −45 degree and for each acquisition, the acquisition plane is moved orthogonal to the −45 degree plane, i.e., moves in the +45 degree plane.

In some examples, the micro-beamformer integrated circuit (IC) 304 can control the array of imaging elements 302 and can perform beam forming for the array imaging elements 302.

In some embodiments, the electrical cable 266 further includes one or more power lines for feeding power to the micro-beamformer IC 304, one or more control lines for communicating control signals to the micro-beamformer IC 304, and one or more signal lines for transferring imaging signals.

In some embodiments, the array imaging elements 302 is a two dimensional array. In some examples, the array imaging elements 302 is symmetric such that it has equal number of rows of imaging elements and columns of imaging elements. In some other examples, the array imaging elements 302 is asymmetric such that it has different number of rows of imaging elements and columns of imaging elements.

In some embodiments, the delay elements in use consist of a number of repeated elements, and the number of these elements determines the maximum available delay. Since the acoustic array may be flip-chip mounted to the micro-beamformer IC 304, all of the processing, including the delay, for any given element can reside in the area occupied by that one element.

In some examples, a plurality of imaging signals, received by the array of imaging elements, are beam formed. The plurality of imaging signals are associated with a plurality of planes between the first plane and the second plane. A 3D volume image is generated from the plurality of imaging signals such that the 3D image corresponds to a volume image between the first plane and the second plane.

Figure 8:
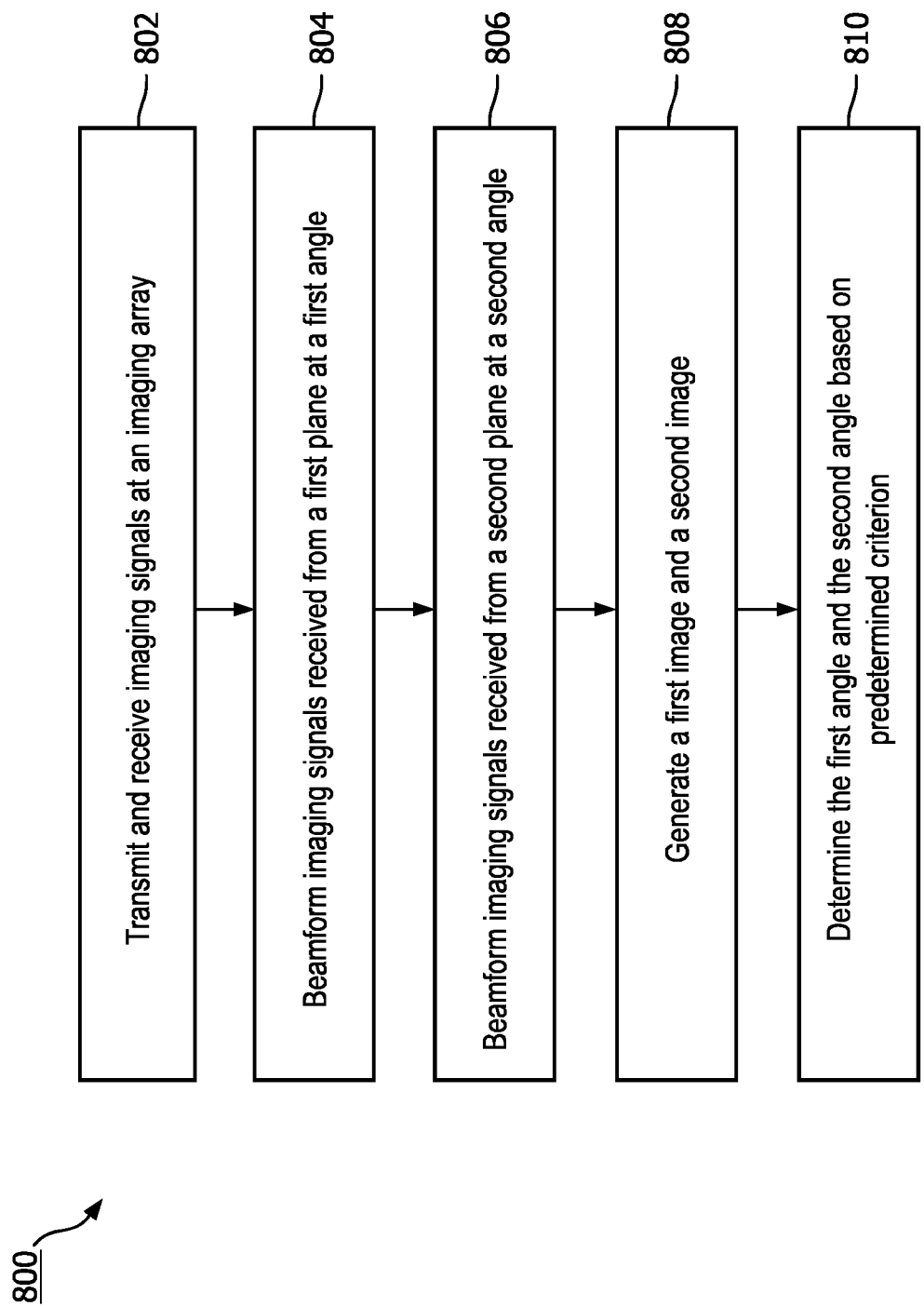
FIG. 8 is a flow diagram of a method of performing intraluminal imaging with an intraluminal device according to aspects of the disclosure.

FIG. 8 provides a flow diagram illustrating a method 800 of intraluminal imaging of a vessel. The method 800 can be performed with reference to FIGS. 1, 2, 3, 4A, and 4B. At step 802, imaging signals are transmitted and received at a side-looking array of imaging elements, e.g., the array of imaging elements 302. The array of imaging elements 302 can be positioned within the distal portion 104 of an intraluminal imaging device 110. In some examples, a micro-beamformer IC 304 is directly coupled to the array of imaging elements 302 and transmits and receives imaging signals, e.g., ultrasound signals. In some examples, the array of imaging elements 302 is an array of ultrasonic transducers.

At step 804 of the method 800 the first imaging signals received by the array of imaging elements 302 are beam-formed. The beamforming can be performed with reference to FIG. 3 such that the micro-beamformer IC 304 can be coupled, e.g., from beneath, to the array imaging elements 302 and can provide the required beamforming delays. The micro-beamformer IC 304 can command the array imaging elements 302 and can transmit and receive signals, e.g., ultrasound signals. The micro-beamformer IC 304 can also include a plurality microchannels delay lines. The micro-beamformer IC 304 can supply the required delays for beamforming from one or more of the microchannels delay lines to the array of imaging elements 302. In some examples, the beamforming is performed during both transmitting and receiving. In some other examples, the beamforming is performed during the receiving. In some examples, the ultrasound signals received by the imaging elements are beamformed by applying the required delays to construct a first beam-formed signal associated with a first plane at a first angle relative to an axial direction of an aperture of the side-looking array of imaging elements.

At step 806 of the method 800 the second imaging signals received by the array of imaging elements 302 are beam-formed. As noted, the beamforming can be performed with reference to FIG. 3. The micro-beamformer IC 304 can supply the required delays to provide beamforming for the second imaging signals such that beamforming is provided by applying the required delays to the signals of each of the imaging elements of the array of imaging elements 302. In some examples, the ultrasound signals received by the imaging elements are beamformed by applying the required delays to construct a second beam-formed signal associated with a second plane at a second angle relative to an axial direction of an aperture of the side-looking array of imaging elements.

At step 808 of the method 800, a first image and a second image are generated. The first image is generated from the first imaging signals and the second image is generated from the second imaging signal. The first image corresponds to a view at first plane and the second image corresponds to a view at the second plane.

At step 810 of the method 800, the first angle and the second angles are determined. In some examples, the angles are determined based on a determined criterion between the first image and the second image. In some examples, the first angle and the second angle are predefined and for example they are set at −45 degree and +45 degree. In some other examples, the angles are determined based on a criterion. The predetermined criterion may constitute a relation between the first image and the second image such as a quality or quantity relationship between the first and second image. For example, the criterion can be related to the resolution of the two images. As noted the typical x-plane images at 0 degree and 90 degree may not have a similar resolution when the aperture of the array of imaging elements 302 is not symmetric, e.g., rather than being square it is rectangular. In some examples, the first angle and the second angle are selected such that the first and second images have comparable resolution and at the same time they are essentially perpendicular to each other, such as +45 degree and −45 degree relative to the longitudinal dimension of the array.

In some examples, the first angle is identical to the 2D plane that was viewed immediately before entering the x-plane mode, and the second angle is as close to orthogonal to the first angle as possible within the constraint that the second angle is not within a pre-determined range of angle around the transverse (short aperture) dimension of the array. At least one of the image planes may be manually adjusted in rotation angle and/or tilt after the system selects the default image planes, and the manual adjustment can include the angle range that was excluded by the default image plane selection. The exclusion angle range for the default position of the second image plane could also be adjusted by the user as a setup parameter, to accommodate the user's tolerance for reduced resolution imaging. As noted, the resolution is noticeably worse but acceptable up to 60 degree, and degrades rapidly from 60 degree to 90 degree. In some examples, the exclusion angle range is from 45 degree to 90 degree. In some other examples, the exclusion angle range is from 60 degree to 90 degree.

In some embodiments, the first angle is selected as an angle corresponding to an angle of a 2D plane viewed immediately prior to this selection. In some examples, the first angle is manually selected. In some embodiments, the second angle is determined as close as possible to orthogonal to the first angle and additionally avoiding the noted exclusion angle range.

In some embodiments, the side-looking array of imaging elements is a phased-array transducer array and the imaging signals are ultrasound signals.

In some examples, the first plane and the second plane are essentially at right angles.

In some embodiments, a connection cable 122 couples the flexible elongate member 102 to a control and processing system 130. The micro-beamformer IC 304 may send the first imaging signals and the second imaging signals through the connection cable 122 to a control and processing system 130 that is configured to construct the first image and the second image.

In some embodiments, the control and processing system 130 is configured to send one or more commands including beam forming commands to the micro-beamformer 304.

As described, for a very asymmetrical aperture, such as a catheter side-looking matrix transducer, x-plane mode can default to ±45 degree planes instead of 0 degree and 90 degree, so both images have good resolution while still being 90 degree apart. The 3D acquisition planes can also be rotated 45 degree for the asymmetrical aperture, so 3D volume rendering and MPR planes have good resolution from either of viewing directions (along the acquisition planes at 45 degree and orthogonal to the acquisition planes at −45 degree). This means that x-plane and 3D/MPR are not oriented the same as the previously viewed single 2D image, which is typically aligned with the long aperture dimension. But this may be a reasonable trade-off to make x-plane and 3D modes more clinically useful.

In some embodiments, systems and methods of the invention provide controls for adjusting the imaging planes or angles. In some examples, the electronic controls for adjusting 2D scan plane rotation angle are buttons on the transducer handle. In some embodiments, the invention provides for controls that are not positioned or available on the disposable catheter or the catheter handle. For example, it may not be desirable to include those controls on the catheter because of cost constraints for a disposable product. In some embodiments, the control for the catheter imaging planes is positioned on the imaging system itself. For example, there can be a control for scan plane rotation angle on the ultrasound console control panel. In some embodiments, systems of the invention provide a control panel that is not associated with the handle or the imaging system. In some examples, the control panel for adjusting the imaging plane could be implemented as a footswitch (such as a dual footswitch, for up and down) operated by the doctor who is manipulating the imaging catheter. In addition to the 2D scan plane rotation angle, the footswitch could also be programmed to control other much-used functions such as x-plane rotation or tilt angle.

Since the imaging system including the console is typically controlled by a third party who is not the doctor but it may be the doctor who controls the ICE catheter, even if the console or a remote control panel was within the doctor's reach, it may not be useful because typically the doctor's hands are fully occupied manipulating the catheters. Continually verbally requesting scan plane rotation angle changes, when the console operator does not know what the doctor wants to see in the image, is a very inefficient work flow. As noted, the footswitch control panel is desirable and solves the problem.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system, comprising:
   an intraluminal imaging device configured to be advanced through a blood vessel of a patient and comprising an array of imaging elements, wherein the array of imaging elements comprises an asymmetric shape with a long axis and a short axis perpendicular to the long axis; and
   a processor configured for communication with the intraluminal imaging device, wherein the processor is configured to:
      select a default setting of a two-plane imaging mode, wherein the default setting comprises:
         a first angle for a first image plane;
         a second angle for a second image plane, wherein the first angle and the second angle are different from one another, wherein the first angle and the second angle are oblique angles relative to at least one of the long axis or the short axis; and
         an exclusion angle range comprising a first plurality of angles, wherein a setting of the exclusion angle range is distinct from a setting of the first angle and a setting of the second angle, wherein the first image plane and the second image plane are excluded from imaging the first plurality of angles inside the exclusion angle range by default such that the first angle and the second angle are each one of a second plurality of angles outside of the exclusion angle range by default, wherein images generated at the first plurality of angles inside the exclusion angle range comprises a lower resolution than images generated at the second plurality of angles outside the exclusion angle range;
      control, based on the default setting, the array of imaging elements to obtain imaging signals associated with the first image plane and imaging signals associated with the second image plane;
      receive a manual adjustment configured to modify the second image plane such that the second angle is changed to be:
         one of the first plurality of angles inside the exclusion angle range; or
         a different one of the second plurality of angles outside the exclusion angle range; and
      control, based on the manual adjustment and not the default setting, the array of imaging elements to obtain imaging signals associated with the modified second image plane.

2. The system of claim 1, wherein the processor is configured to control the array of imaging elements to simultaneously obtain the imaging signals associated with the first image plane and the imaging signals associated with the second image plane.

3. The system of claim 1, wherein an axial direction of the array of imaging elements is aligned with the long axis.

4. The system of claim 1,
   wherein the array of imaging elements comprises a phased-array transducer array,
   wherein the imaging signals associated with the first image plane and the imaging signals associated with the second image plane comprise ultrasound signals.

5. The system of claim 1, wherein the intraluminal imaging device comprises:
   a flexible elongate member comprising a proximal portion and a distal portion; and
   an imaging assembly mounted within the distal portion of the flexible elongate member, wherein the imaging assembly comprises:
      the array of imaging elements; and
      a micro-beamformer integrated circuit (IC) coupled to the array of imaging elements, wherein the micro-beamformer IC is configured to beamform the imaging signals associated with the first image plane and the imaging signals associated with the second image plane.

6. The system of claim 5, wherein the micro-beamformer IC includes a plurality of microchannel delay lines that are configured to apply a plurality of predetermined delays to the imaging signals associated with the first image plane and the imaging signals associated with the second image plane.

7. The system of claim 5,
wherein the micro-beamformer IC is further configured to beamform a plurality of groups of imaging signals received by the array of imaging elements,
wherein each group of the plurality of groups of imaging signals is associated with a plane between the first image plane and the second image plane,
wherein the processor is configured to generate a three-dimensional (3D) volume image based on the plurality of groups of imaging signals.

8. The system of claim 1, wherein the first angle and the second angle are perpendicular.

9. The system of claim 8, wherein the first angle comprises +45 degree relative to the long axis and the second angle comprises −45 degree relative to the long axis.

10. The system of claim 1,
wherein the processor is configured to:
generate a first image based on the imaging signals associated with the first image plane and a second image based on the imaging signals associated with the second image plane; and
output the first image and the second image to a display,
wherein the first image and the second image comprise a same resolution.

11. The system of claim 10,
wherein the processor is configured to output, to the display, a modified second image based on the imaging signals associated with the modified second image plane,
wherein, when the second angle is changed based on the manual adjustment to be the different one of the second plurality of angles outside the exclusion angle range, the first image and the modified second image comprise different resolutions.

12. The system of claim 10, wherein the processor is configured to:
control the array of imaging elements to obtain imaging signals associated with a third image plane aligned with the long axis;
generate a third image based on the imaging signals associated with the third image plane aligned with the long axis; and
output, to the display, the third image adjacent to at least one of the first image or the second image.

13. A method, comprising:
selecting, with a processor in communication an intraluminal imaging device comprising an array of imaging elements, a default setting of a two-plane imaging mode, wherein the array of imaging elements comprises an asymmetric shape with a long axis and a short axis perpendicular to the long axis, and wherein the default setting comprises:
a first angle for a first image plane;
a second angle for a second image plane, wherein the first angle and the second angle are different from one another; and
an exclusion angle range comprising a first plurality of angles, wherein a setting of the exclusion angle range is distinct from a setting of the first angle and a setting of the second angle, wherein the first image plane and the second image plane are excluded from imaging the first plurality of angles inside the exclusion angle range by default such that the first angle and the second angle are each one of a second plurality of angles outside of the exclusion angle range by default, wherein images generated at the first plurality of angles inside the exclusion angle range comprises a lower resolution than images generated at the second plurality of angles outside the exclusion angle range;
controlling, with the processor and based on the default setting, the array of imaging elements to obtain imaging signals associated with the first image plane and imaging signals associated with the second image plane, wherein the first angle and the second angle are oblique angles relative to at least one of the long axis or the short axis;
receiving, with the processor, a manual adjustment configured to modify the second image plane such that the second angle is changed to be:
one of the first plurality of angles inside the exclusion angle range; or
a different one of the second plurality of angles outside the exclusion angle range; and
controlling, with the processor, the array of imaging elements to obtain imaging signals associated with the modified second image plane, based on the manual adjustment and not the default setting.

* * * * *